United States Patent [19]

Moore

[11] Plant 4,029

[45] Mar. 29, 1977

[54] MINIATURE ROSE PLANT

[76] Inventor: Ralph S. Moore, 2519 E. Noble Ave., Visalia, Calif. 93277

[21] Appl. No.: 672,742

[22] Filed: Apr. 1, 1976

[51] Int. Cl.[2] ..... A01H 5/00
[52] U.S. Cl. ..... Plt./7
[58] Field of Search ..... Plt./7

*Primary Examiner*—Robert E. Bagwill

EXEMPLARY CLAIM

1. A new and distinct variety of miniature rose plant of hardy, dwarf, bushy, upright, much branched habit, as illustrated and described, characterized by buds and flowers which are striped (variegated) in varying proportions of red and white of a color combination resembling Ferdinand Pichard (an older H.P. variety) and a plant habit somewhat taller than broad, the bud and flower form resembling Baby Darling (miniature — U.S. Plant Pat. No. 2,582) and the size similar to New Penny (miniature — not patented); and further characterized by a plant which is vigorous and compact, the shoots and branches having fairly short internodes, said plant being easy to propagate from cuttings (often blooming in small pot when plant is not over 6 inches tall) with small semi-glossy foliage, an abundance of bloom, with flowers borne singly or several to the stem in loose clusters.

1 Drawing Figure

The present invention relates to a new and distinct variety of hardy, dwarf, shrub type rose plant of the miniature class; the variety being primarily characterized — as to novelty — by striped (or variegated) red and white buds and flowers which in general color effect are similar in color to Ferdinand Pichard, an older hybrid perpetual variety (not patented).

The variety is further characterized by:

An abundance of bloom, with flowers borne singly or several to the stem in loose clusters.

Sweet wild rose fragrance.

A plant which is vigorous, of rounded upright shape and with semi-glossy, small foliage with pointed leaflets; the buds and flowers being similar in form to Baby Darling (miniature — U.S. Plant Pat. No. 2,582) and in size to the variety New Penny (miniature — not patented).

The plant, which has a normal height of 16–20 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Little Chief, miniature, not patented as the seed parent and an un-named seedling (Little Darling — U.S. Plant Pat. No. 1,581, expired × Ferdinand Pichard, H.P. — not patented), as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds, and flowers.

Referring now specifically to the new and distinct variety of miniature rose plant, the following is a detailed description thereof in outline; all major color plate identifications being by reference to the British Colour Counsel Horticultural Colour Chart, except where common terms of color definition are employed.

Type: Hardy; dwarf; shrub (bushy, upright plant); seedling; greenhouse; outdoors; cut flowers; garden decoration; potted plant.

Class: Miniature. Variety name: 'Stars 'N Stripes.'

Flowers: Continuity; continuous — repeat bloom all season. Fragrance; sweet, wild rose.

Flowers borne: Singly and several together (3 to 5) on tips of main shoots and on shorter lateral shoots.

Quantity of bloom: Abundant both outside and in greenhouse.

Bud: Peduncle — medium length; slender but sturdy; erect; medium green, sometimes tinted bronze (outdoors); hairs — usually none. Before calyx breaks; size — small. Form: long; pointed with few foliaceous appendages and few or no hairs on surface of bud; with foliaceous parts extending beyond the tip of the bud equal to one-half or less of its length. Color — medium green, occasionally tinted with bronze (outdoors). As calyx breaks, color — medium red, or white with red stripes (or red streaks) — varies from one bud or flower to another; opens: same general color; variegated — red and white; size — small.

Bloom: Size when fully open — small, averaging about 35 mm. Petalage — double — 15 to 20 petals, arranged regularly plus sometimes several small petaloids. Form — flat at first, becoming more open in the center, with petals rolled loosely outward, and later at maturity open with petals folded at tips to give a pointed effect and rolled loosely outward and downward. Open flowers show yellow stamens which give pleasing contrast with petal color.

Petals: Fairly thick; satiny on inside and on outside surface. Shape — outside petals, broad lanceolate with rounded tip; intermediate — broad lanceolate with rounded tip; inside — lanceolate with rounded tip.

Color: Newly opened flower from a plant grown in plastic greenhouse (Mar. 1976), Visalia, Calif.

*Outside petal.*—Outside surface — basically white with red areas from inside surface bleeding through to give a red shade similar to Rose Bengal 25/1 and with small yellow area at base; inside surface — white overlaid with red similar to Chrysanthemum Crimson 824/2, in varying degree, with some areas all red, some pinkish and some white or near white — with a bit of yellow at base.

*Intermediate petal.*—Outside surface — similar to outside petal. Inside surface — similar to outside petal.

*Inner petal.*—Outside surface — same as intermediate petal; inside surface — same as intermediate petal. General color effect newly opened flowers — white with red stripes. Three days open — color similar to newly opened flowers but lighter color. Behavior — as flowers age the red portions may become lighter shade of red. Spent petals drop off. Flower longevity (Oct. 1975) — plant in pot 4–5 days or longer. Cut flowers at living room temperature 3 days.

Reproductive Organs:

*Stamens.*—Abundant, arranged regularly about pistil.

*Filaments.*—Varying length, light yellow.

*Anthers.*—Well formed; yellow.

*Pollen.*—Little or none.

*Pistils.*—Average number.

Styles.—Fairly even; medium length; bunched; color — near white.

*Stigma.*—Nearly white.

*Ovaries.*—All enclosed in calyx.

*Hips.*—Few.

*Sepals.*—Permanent; spear shaped; recurved.

*Seed.*—Few.

Foliage:

*Leaves.*—Compound of five (sometimes three or seven) leaflets; abundant; quite small; leathery; semi-glossy.

*Leaflets.*—Shape; broad, nearly oval; apex acute; base rounded or rounded acute. Margin serrate. Color: medium green; new growth — normal (medium) green. Rachis: medium strength; upper side may have a few tiny short hairs, grooved; underside sparsely thorny with few or no tiny prickles. Stipules: medium long; narrow to medium width; medium length narrow points which turn out usually at about 45°.

Growth:

*Habit.*—Dwarf; bushy; upright; much branched.

*Growth.*—Free vigorous; internodes short.

*Canes.*—Medium; slender; sturdy.

*Main stems.*—Color: light to medium green.

*Thorns.*—Few — usually small; hooked slightly downward; color — brown. Prickles — none. Hairs — none.

Branches: Color — light to medium green. Thorns — few; short length; slender; nearly straight. Medium to short oval base. Prickles — none. Hairs — none.

The miniature rose plant and its flowers as herein described may vary in slight detail due to climatic, soil and cultural conditions under which the variety may be grown; the present description being of the variety as grown at Visalia, Calif. The following is claimed:

1. A new and distinct variety of miniature rose plant of hardy, dwarf, bushy, upright, much branched habit, as illustrated and described, characterized by buds and flowers which are striped (variegated) in varying proportions of red and white of a color combination resembling Ferdinand Pichard (an older H.P. variety) and a plant habit somewhat taller than broad, the bud and flower form resembling Baby Darling (miniature — U.S. Plant Pat. No. 2,582) and the size similar to New Penny (miniature — not patented); and further characterized by a plant which is vigorous and compact, the shoots and branches having fairly short internodes, said plant being easy to propagate from cuttings (often blooming in small pot when plant is not over 6 inches tall) with small semi-glossy foliage, an abundance of bloom, with flowers borne singly or several to the stem in loose clusters.

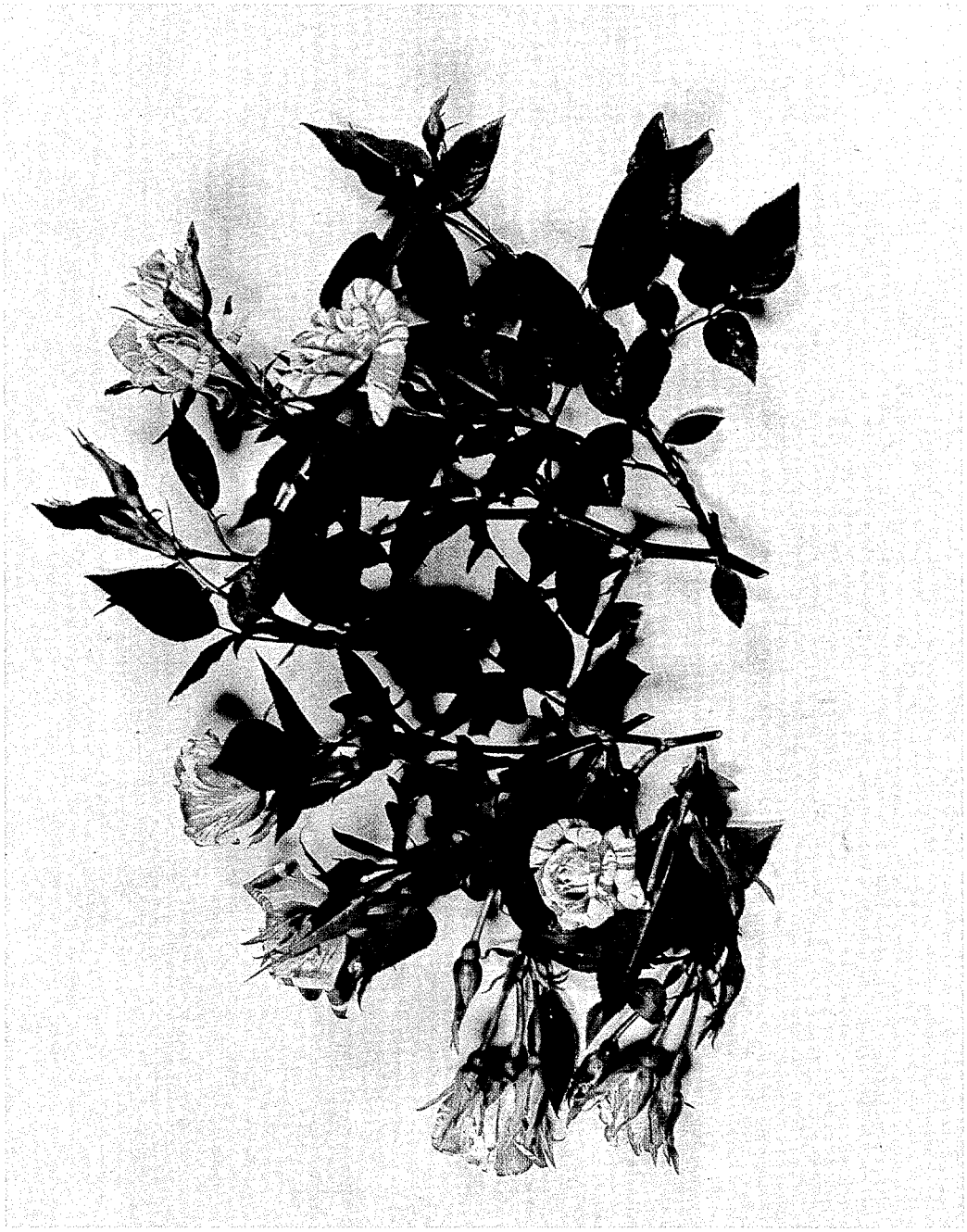

* * * * *